United States Patent [19]

Glasser et al.

[11] 3,976,050

[45] Aug. 24, 1976

[54] DEVICE FOR ADSORBING EXHALED RADIOACTIVE GASES AND PROCESS

[75] Inventors: Herman Glasser, New Hyde Park; Patrick F. Panetta, East Islip, both of N.Y.

[73] Assignee: Nuclear Associates, Inc., Carle Place, N.Y.

[22] Filed: Nov. 18, 1974

[21] Appl. No.: 524,457

[52] U.S. Cl. .............................. 128/2 A; 55/66; 55/74; 128/2.08
[51] Int. Cl.² ...................................... A61B 5/08
[58] Field of Search ............... 128/2 A, 2.08; 55/66, 55/74

[56] References Cited
UNITED STATES PATENTS

| | | | |
|---|---|---|---|
| 1,519,932 | 12/1924 | Reich | 55/74 X |
| 2,793,507 | 5/1957 | Hnilicka | 55/66 X |
| 2,835,343 | 5/1958 | Wolff et al. | 55/66 |
| 3,517,521 | 6/1970 | Emerson | 55/66 X |
| 3,720,043 | 3/1973 | Kovach | 55/74 |
| 3,769,967 | 11/1973 | Jones et al. | 128/2.08 |
| 3,871,841 | 3/1975 | Queiser et al. | 55/66 |
| 3,871,842 | 3/1975 | Queiser et al. | 55/66 X |
| 3,881,463 | 5/1975 | Lemon | 128/2 A |

Primary Examiner—Kyle L. Howell
Attorney, Agent, or Firm—Lilling & Siegel

[57] ABSTRACT

Sorption means are provided for sorbing radioactive gases, as in the exhalations of a living subject, especially for nuclear diagnostic test studies, comprising means for adsorbing the radioactive gas onto activated carbon, the carbon being contained in a plurality of independent, series-connected, chambers. The sorption means are especially adapted for the adsorption of radioactive inert gases such as xenon-133 ($^{133}$Xe). There can also be provided indicator means for indicating the flow-through of xenon comprising an indicator which changes color upon contact with xenon, such as dioxygenylhexafluoroantimoniate.

14 Claims, 7 Drawing Figures

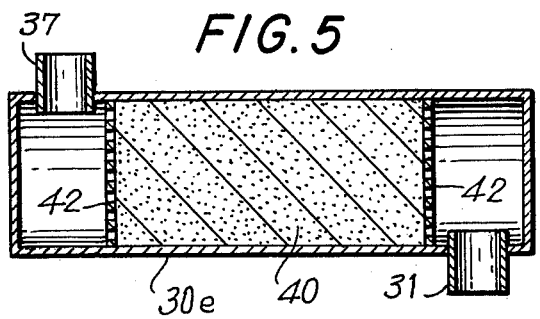
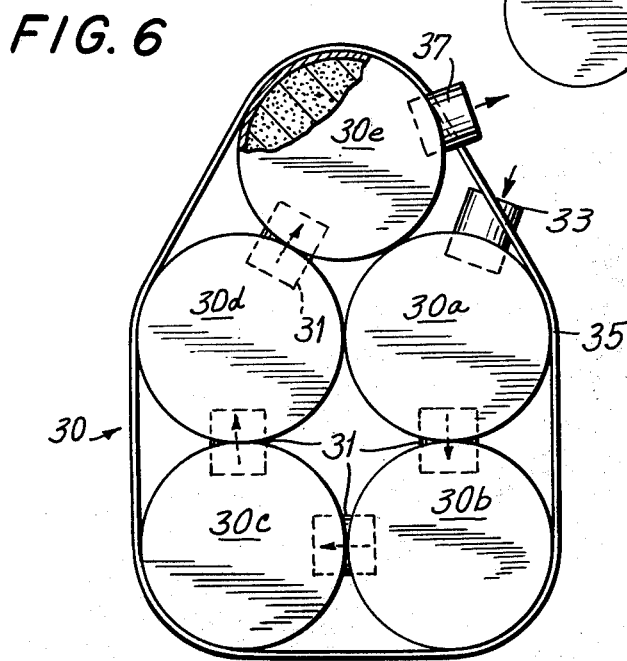
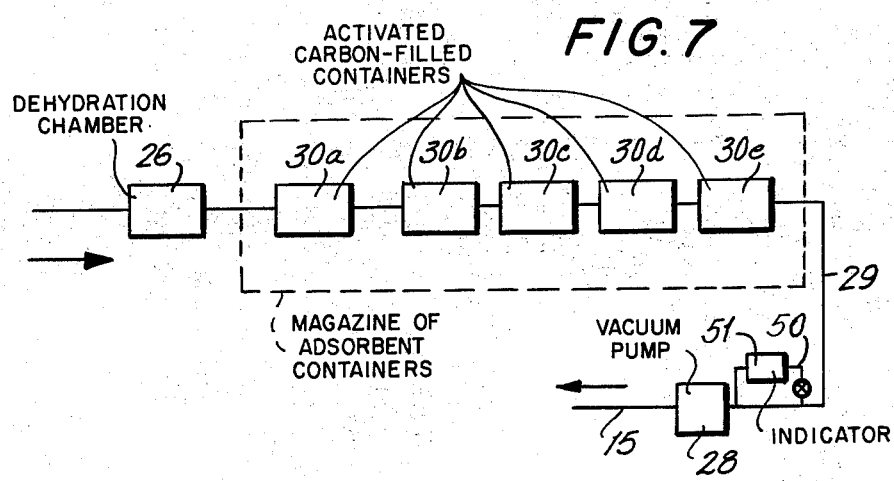

DEVICE FOR ADSORBING EXHALED RADIOACTIVE GASES AND PROCESS

This invention relates to breathing equipment, specifically for diagnostic test purposes, utilizing a radioactive noble gas, especially radioactive xenon, wherein the xenon is adsorbed and prevented from being exhausted into the atmosphere in its radioactive condition.

A commonly used diagnostic tool for determining the functionality of a subject lung, used during circulatory and respiratory studies, involves the inhalation of a gaseous mixture to which has been added a radioactive gas such as xenon-133. Generally, in carrying out such tests, the subject breathes in the radioactive xenon-containing gas mixture until the amount of such xenon in his lungs reaches an equilibrium conditon. At that point, a valve is turned and ambient air is breathed, which serves to wash out the radioactive xenon from the patient's lungs. It is during the exhalation of the xenon from the lungs that care must be taken to prevent contamination of the intermediate surroundings.

Generally, present statutory requirements of the United States Atomic Energy Commission, or of other local jurisdiction, require that the concentration in a certain controlled zone be not greater than $1 \times 10^{-5} \mu \lambda$ Ci/cm$^3$ for Xenon-133. The art has accomplished this by having the subjects continuously exhale into an exhaust line, which is connected to a system for adsorbing all inert gases in the subject's exhalations. In accordance with conventional practice, gas traps have been utilized for collecting the radioactive xenon expired from the subjects during circulatory and respiratory studies. Such systems have included a breathing bag; means for dehumidifying the expired air, e.g. a solid dessicant; a xenon trap connecting eight chambers in parallel, filled with an activated carbon, and a vacuum pump. The dehumidifying chamber and the eight chambers are surrounded by a radioactive shield such as lead. As breath is expelled, and after data on the exhalation have been collected, the exhaled or expired air is drawn by the vacuum pump through the breathing bag and dehumidifier and into one of the eight charcoal-filled chambers. All xenon contained in the dried, expired air is adsorbed onto the activated carbon, and the remaining gas can then be vented to the atmosphere. Such commercially available units have generally been designed to accept the complete exhalations during "washout" of a single patient. A second chamber is used for the next patient. These commercial units are allegedly designed so that if the eight chambers are used in succession to collect the expired air, the radioactive xenon sorbed in the previously utilized chambers decays to a safe level. It is then anticipated that the first chamber can then be reutilized after the eighth chamber has been used in continuing rotation. Unfortunately, the results have not been up to expectations and the life of such units containing the eight parallel chambers of activated charcoal adsorbent has been limited.

A further problem has been that the art had no way of knowing when such a gas trap is saturated and unable to fulfill its function of adsorbing xenon except by the measurement of radioactivity in the vented air.

In accordance with the present invention, it has now been determined that the useful life of a radioactive xenon gas trap, utilizing activated carbon adsorbent, can be substantially increased, without any increase in the amount of adsorbent utilized, by connecting the adsorbent-filled containers in series, such that the expired air passes through each of the containers before being vented to the atmosphere. It is necessary that the adsorbent solids in each container be completely out of contact and separated from the adsorbent solid in the adjacent containers, the only connection being through a fluid flow conduit means, empty of solid adsorbent.

As a further means for insuring that there is no contamination of the surroundings by inadvertent venting of the radioactive xenon, an indicator means is provided downstream of the final adsorbent container. Generally the indicator is in parallel with the mainstream and is exposed only to a sample of the vented xenon-free air.

In operation, a uniform, substantially constant low flow rate is obtained over the adsorbent solid by the use of a small pump, generally a vacuum pump at the exhaust end of the gas trap. Preferably, the adsorption is carried out at ambient temperatures.

It has been found that as few as three independent adsorbent-containing cartridges, in series connection, results in a substantial increase in the life of the gas trap utilizing a given amount of activated adsorbent material compared to the parallel connected cartridges of the prior art, the reason why this occurs is not completely understood. However, it is believed that by utilizing a series of completely independent cartridges, the overall capacity of a given amount of adsorbent is increased. This is achieved by separating the adsorbent into individual units such that the first unit is first saturated before any xenon passes into the second unit. As the xenon passes through the first unit into the second unit, the radioactive xenon adsorbed on the first unit decays. The decay product of the radioactive xenon-133 is radioactively inert cesium, i.e. a solid material.

Any inert xenon which remains in the earlier, or upstream, adsorbent container can be exchanged, by the usual equilibrium procedures, with the radioactive xenon passing through to the subsequent chambers. Further as the radioactive xenon decays, there is room for additional xenon in the upstream chambers. As a result of this continuing system, the total life of the series of independent cartridges is greatly enhanced over that of an equal amount of adsorbent in a parallel system of individual adsorbent cartridges.

In the verbal description set forth below and in the accompanying drawings, the elements of the apparatus of this invention are shown and described in a highly simplified form and generally in an essentially symbolic manner. Appropriate structural details for actual operation are readily known and understood and need not be set forth herein, as they are not part of the present invention. Generally, the individual adsorbent cartridges, the dehumidifying, or drying, chamber and vacuum pump are conventional in the art for the present purpose. Similarly, the radioactive shielding is provided in sufficient quantity to maintain the ambient radiation level below accepted uncontrolled area levels.

The following examples set forth in the accompanying drawings and verbal text merely exemplify certain advantageous embodiments of the apparatus in accordance with the present invention. They are not to be taken as limiting of the scope of the invention, but are merely exemplary thereof.

FIG. 4 is a drawing, in perspective of the combination of adsorbent cartridges in series.

FIG. 5 is a longitudinal cross section through one cartridge.

FIG. 6 is a front elevation view of the cartridges of FIG. 4; and

FIG. 7 is a diagrammatic sketch, showing the flow of air through the gas trap of the present invention.

Figure 1:
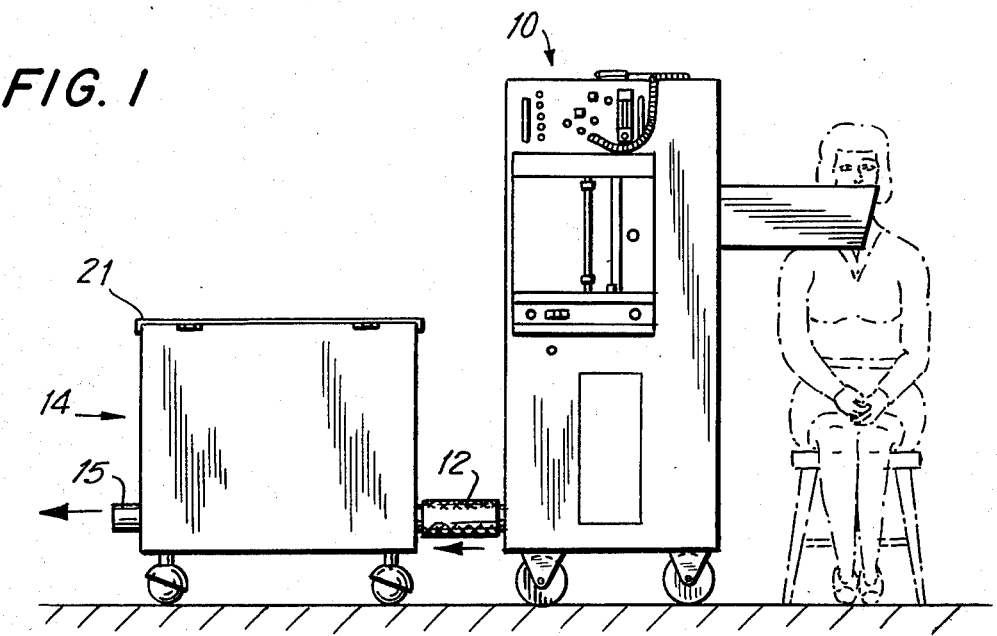
FIG. 1 is an overall sketch of a diagnostic system, including the gas trap of the present invention, and indicating the position of the subject to be diagnosed.

Referring to FIG. 1, a diagnostic subject, indicated in phantom lines, is shown in operating position relative to a conventional lung-function unit 10 which includes collection means designed and adapted to collect lung exhalations from a living subject. The lung-function unit 10, which typically includes a mouthpiece, may be of the type made available by Nuclear Associates, Inc. and described in its Product Bulletin NA-125C (10/10/73). However, the specific constructional details of the lung-function unit 10, as well as the collection means thereof, does not form a critical part of the present invention. The lung-function unit is in fluid flow connection via conduit 12 with a xenon adsorption unit, indicated generally by the numeral 14, in accordance with the present invention. The dried effluent gas, stripped of its radioactive component, is vented to the atmosphere via exhaust line 15.

Figure 2:
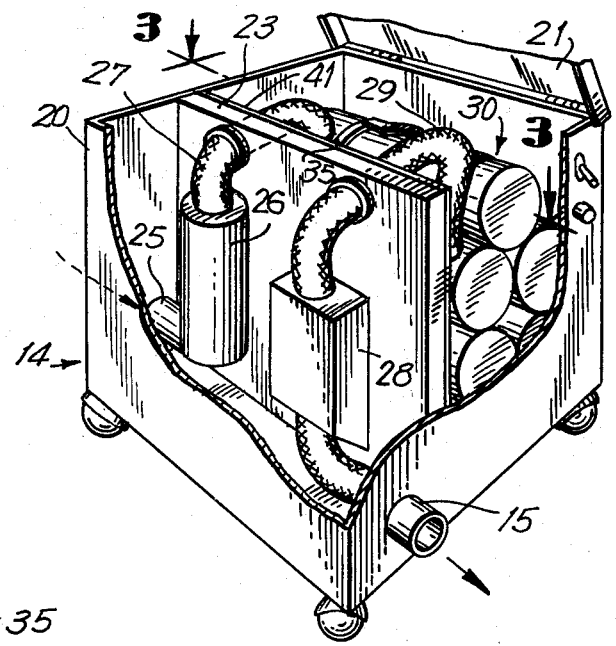
FIG. 2 is a partially cut-away drawing, in perspective, of the gas trap in accordance with the present invention.
Figure 3:
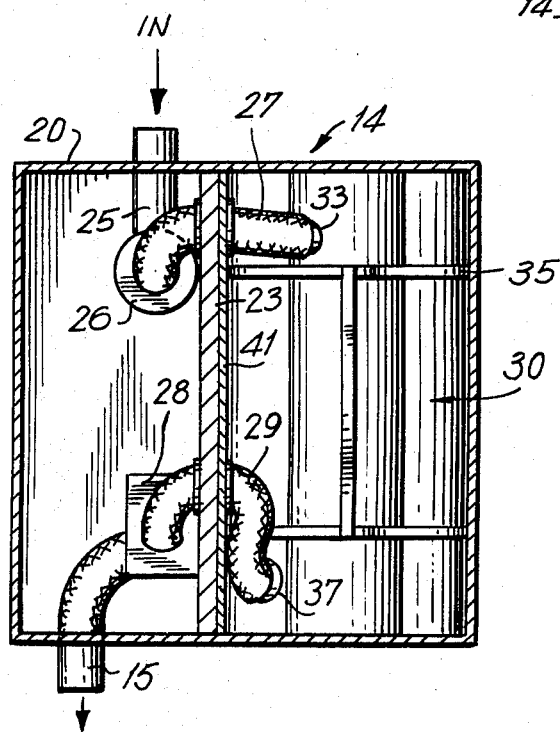
FIG. 3 is a cross-sectional view along lines 3—3 of FIG. 2.

As shown in FIGS. 2 and 3, the xenon adsorbent device comprises an outer case 20 and a hinged top for the case 21. The interior of the case is divided into two compartments by a lead shield 23. The exhaled air enters through conduit 12 in the wall of the case 20 and into the first compartment within the unit. The inlet 12 is in fluid connection through conduit 25, first with a dehydration unit 26, containing a solid dessicant, or water absorbent means, such as activated silica. In the second chamber within the case 20, on the other side of the lead shield 23, is located the series of activated carbon-filled containers generally indicated by the numeral 30. The series of containers is shown in greater detail in FIGS. 4 and 6. As shown most clearly by FIG. 6, the containers 30a, 30b, 30c, 30d and 30e, are connected in series, in that order, by short lengths of tubing 31 connecting the adjacent containers. Care must be taken to assure that substantially no direct physical contact is made between the activated carbon contained in each of the various containers. The exhaust from the dehydration chamber 26 is connected via conduit 27, which passes through the lead shield 23, to the inlet 33 to the bundle of adsorbent cartridges. The five adsorbent cartridges are shown as being held together by a pair of straps 35 to insure that there is no relative movement among the containers which could disrupt the fluid connections 31. The exhaust 37, from the last adsorbent cartridge 30e, is connected via conduit 29 to a vacuum pump 28, the exhaust of which is in turn connected to the vent 15.

Fluid flow connection between successive containers 30 can be maintained, without contact of adsorbent, utilizing, for example, the cartridge construction shown in FIG. 5. The container 30e, comprises a central compartment substantially filled with the solid adsorbent 40 and bounded by porous disks 42. The porous disks 42 permit the passage of gases but prevent the passage of the adsorbent particles. The plenum spaces at each end of the container 30e are connected to the preceding container, via conduit 31 and to the exit, via conduit 37, respectively.

The second compartment within the case 20 is fully lined with a lead sheet 41 around the sides and floor, such that the magazine of adsorbent cartridges 30 is completely surrounded by a lead shield. Preferably, that portion of the cover 21, which, when closed, is directly above the second compartment, is also lined with a lead shield. Thus, the compartment containing the adsorbed radioactive xenon gas is completely shielded by a radioactive shield from the immediate surroundings. Lead is generally considered to be the best radioactive shielding material, however, if desired, other dense materials can be substituted therefor.

The vacuum pump is utilized to draw a continuous flow of expired air through the adsorption cartridges at a substantially uniform flow rate. The flow rate must be so designed as to result in a sufficient residence time within the cartridge to insure that all of the xenon is adsorbed before being vented into the atmosphere.

In the example shown in the drawings, the cartridge magazine 30 contains five cartridges. More generally, however, as stated above, at least three cartridges will result in a substantial improvement as compared to utilizing a single cartridge containing the same amount of adsorbent or a plurality of cartridges in parallel connection, for adsorbing xenon. The maximum number of cartridges is limited only by the available or preferred size of the xenon adsorption case. A further advantage of utilizing the series-connected cartridge is the greater compactness of the device compared to operating with a device containing a similar amount of adsorbent in a single cartridge or in parallel cartridges. Accordingly, preferably from four to about ten cartridges and most preferably from four to eight cartridges are utilized.

As an example of a suitable xenon trap which can be operated in conjunction with a conventional lung-function unit, the following dimensions would be applicable. The vacuum pump can be set to operate at approximately 5 liter/min. The five cartridges containing the activated charcoal would each be generally cylindrical in shape, approximately 10 inches long and 4 inches internal diameter. The cartridge can be made, for example, of any synthetic resin, e.g. nylon, polypropylene, etc. Alternatively of course, if desired, a metal pipe, for example, lead or steel, could be utilized.

The second chamber within the unit as shown in FIG. 1, i.e. that section surrounding the adsorbent magazine, is shielded with a ⅛ inch lead barrier completely surrounding the cartridge magazines. The individual cartridges within the cartridge magazine 30 (of FIG. 2 and FIGS. 4 and 6) are connected so as to ensure that the gases flow along substantially the entire length of the cartridge, and are distributed evenly throughout its cross section. The activated carbon utilized, preferably includes alkali metal deposited thereon, such as sodium or potassium or cesium. The activated carbon should be in granular form. The selection of a suitable activated carbon however, is conventional in the art and the general practice can be followed with this invention. See, for example, U.S. Pat. No. 2,835,343.

In order to obtain the optimum life from the adsorption means in accordance with the present invention, it is preferred that the use to which the device is placed be restricted; for example, for the apparatus of the size defined above, when used in conjunction with a lung-function unit, the gas trap should preferably be limited to use for the testing of about twelve average size adult patients per week. Greater use could significantly decrease the life-span of the adsorbent as regard total number of patients serviced. This same limitation as noted, is also placed upon the use by the prior art of apparatus where the cartridges have been placed in parallel.

As shown in the flow diagrams of FIG. 7, when an indicator is desired to be used, a side, or slip, stream 50 is utilized for passage of a relatively small portion of the expired, dried xenon-adsorbed air to ensure that all the xenon has in fact been absorbed into the cartridges. When the indicator 51 utilized contains dioxygenylhexafluoroantimoniate, a solid, as the indicator material, the indicator turns a bright yellow when a noble gas is present. Although generally an initial indication is most likely non-radioactive xenon or other noble gas, to ensure that there is substantially no escape of radioactive material into the atmosphere, the cartridge pack is preferably changed at that time.

The embodiments and examples set forth hereinabove, are intended to be purely exemplary of the invention defined herein. The scope of the invention and the protection to which the invention is given under law shall be determined by the appended claims which follow.

The patentable embodiments of this invention which are claimed are as follows:

1. An adsorption unit for the adsorption of a noble radioactive gas from a gas mixture, especially the exhalations from an animal, the unit comprising an outer case having an inner compartment; a portable cartridge magazine removably receivable within said compartment and comprising a plurality of at least three closed chambers, each chamber containing activated carbon solid adsorbent for the radioactive gas, the plurality of chambers being in fluid flow series connection, but the solid adsorbent within each chamber being out of direct contact with the solid adsorbent in any other chamber; an inlet to the first, or upstream chamber; (and) an outlet from the last or downstream chamber; and radioactive shielding material associated with at least some of the wall portions of said outer case, whereby said outer case forms a storage unit which substantially confines radiation emanating from said cartridge magazine, said cartridge magazine being removable from said outer case and replaceable by another like cartridge magazine upon the expiration of the life span thereof.

2. The adsorption unit of claim 1, wherein the activated carbon is a particulate, activated carbon, including an alkali metal activator, and which is active to selectively adsorb noble gases from air.

3. The adsorbtion unit of claim 2, comprising, in addition, collection means designed and adapted to collect lung exhalation from a living subject; a moisture adsorbing means to remove moisture from any gasses passing therethrough, in fluid flow connection with the exhalation collection means and the inlet to the first, or upstream, chamber; and pump means for causing the flow of the exhalation gas mixture through the series-connected chambers and moisture-removal means.

4. The adsorption unit of claim 3 comprising at least four chambers containing the solid adsorbent.

5. The adsorption unit of claim 4, comprising from about 4 to about 10 chambers containing solid adsorbent.

6. The unit of claim 1, further comprising indicator means for providing an indication of the condition or expired life-time of said portable cartridge magazine.

7. The adsorption unit of claim 6, where the unit is intended to adsorb radioactive xenon and where the indicator means is dioxygenylhexafluoroantimoniate.

8. The adsorption unit of claim 1, wherein said outer case includes means for making the same mobile.

9. The adsorption unit of claim 1, wherein the interior of said outer case is divided into two compartments.

10. The adsorption unit of claim 9, wherein said portable cartridge magazine is housed in only one of said two compartments.

11. The adsorption unit of claim 10, further comprising a moisture adsorbing means in fluid flow connection with said inlet to the first, or upstream, chamber for removing moisture from gases passing therethrough, said moisture adsorbing means being housed within the other of said two compartments.

12. The adsorption unit of claim 10, further comprising a vacuum pump in fluid flow connection with said outlet from said last or downstream chamber.

13. The adsorption unit of claim 9, wherein said two compartments are separated by a lead shield.

14. The adsorption unit of claim 1, wherein said radioactive shielding material completely lines said compartment to thereby completely surround said portable cartridge magazine.

* * * * *